United States Patent [19]

Obermeier et al.

[11] 4,013,628
[45] Mar. 22, 1977

[54] PROCESS FOR THE PREPARATION OF INSULIN, ANALOGS AND DERIVATIVES THEREOF

[75] Inventors: Rainer Obermeier, Hattersheim (Main); Rolf Geiger, Frankfurt am Main, both of Germany

[73] Assignee: Hoechst Aktiengesellschaft, Frankfurt am Main, Germany

[22] Filed: Aug. 14, 1975

[21] Appl. No.: 604,667

[30] Foreign Application Priority Data

Aug. 16, 1974 Germany .......................... 2439296

[52] U.S. Cl. ............................................ 260/112.7
[51] Int. Cl.² ................ A61K 37/26; C07C 103/52
[58] Field of Search ................................ 260/112.7

[56] References Cited

UNITED STATES PATENTS

| | | | |
|---|---|---|---|
| 3,883,496 | 5/1975 | Geiger ............................. | 260/112.7 |
| 3,883,500 | 5/1975 | Geiger et al. .................... | 260/112.7 |
| 3,884,897 | 5/1975 | Geiger et al. .................... | 260/112.7 |
| 3,907,763 | 9/1975 | Brandenburg et al. ......... | 260/112.7 |

*Primary Examiner*—Lewis Gotts
*Assistant Examiner*—Reginald J. Suyat
*Attorney, Agent, or Firm*—Curtis, Morris & Safford

[57] ABSTRACT

A process for the manufacture of insulin and derivatives thereof by treating an insulin derivative, wherein the A-chain is cross-linked with the B-chain by means of a sulfonyl diethyl-bisoxycarbonyl bridge and the B-chain may contain an acyl group in the 1-position, with alkali metal hydroxides or quaternary organic bases having a pH value of more than 13.

2 Claims, No Drawings

PROCESS FOR THE PREPARATION OF INSULIN, ANALOGS AND DERIVATIVES THEREOF

The present invention relates to a process for the preparation of insulin, analogs and derivatives thereof.

The process of the invention comprises treating a compound of the general formula I

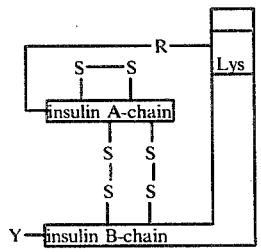

(I), in which Y represents a hydrogen atom or an acyl group, and R represents the sulfonyldiethyl-bisoxycarbonyl radical (SDC radical)

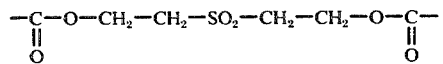

with alkali metal hydroxides or quaternary organic bases having a pH value of more than 13.

According to Biochem. Biophys. Res.Commun.55 (1973), page 60, insulin may be prepared from its chains by linking the α-amino group of the A-chain and the ε-amino group of the B-chain to each other by means of an α,α'-diamino-dicarboxylic acid, closing the disulfide bridges of the insulin corresponding to its formula by dehydrogenation, and finally splitting off the α,α'-diamino-dicarboxylic acid by Edman degradation.

By this process, the two chains of insulin were combined for the first time with a high yield. The Edman degradation was also successful although a certain loss in yield could not be avoided.

According to the process of the invention, the two chains of insulin can now be combined in the same high yield. However, the yields obtained when the bridging reagent is split off are higher than those obtained by the method described above, as the splitting is effected in a single very fast reaction via a β-elimination mechanism with a base as catalyst. In this process the yield is hardly affected by side-reactions and their by-products, since they are rather insignificant. Thus, the purification of the reaction product is also simplified.

While the Edman degradation also splits off the first amino acid of the B-chain, for example phenyl-alanine, unless the α-amino group is provided with a protective group, this is not the case if the SCD radical is used, it may, however, be advantageous in this case, too, to protect the α-amino group of the B-chain, in order to ensure a smooth reaction.

The principle of the reaction in the preparation of the compounds of the general formula I by successive linking of the bifunctional bridge member R to the A- and/or B-chains of the insulin has already been disclosed in the above-mentioned literature as well as in German Offenlegungsschrift No. 2,252,147.

For preparing the compounds of the formula I, an insulin A-chain, the SH groups of which are blocked by one of the known S-protective groups, for example trityl, diphenyl-methyl, S-alkyl having from 1 to 4 carbon atoms, picolyl, acetamidomethyl or sulfonate, is reacted with an excess amount of a compound of the general formula II

in which R has the meaning given above, and OV represents the radical of an ester of the sulfonyldiethyl-bisoxycarbonyl component, for example of the N-hydroxy-succinimide ester, nitrophenyl ester, trichlorophenyl ester, pentachlorophenyl ester, or pentafluorophenyl ester.

The reaction yields compounds of the general formula III

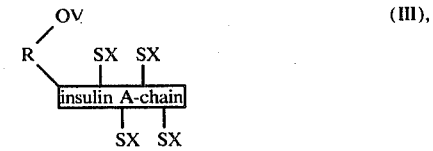

in which X represents an S— protective group. As a solvent for this reaction, dimethylsulfoxide (DMSO) or a dialkyl carboxylic acid amine, especially dimethylformamide (DMF), or phosphoric acid tris-dimethyl amide, is preferably used. The reaction may be carried out at room temperature, but a slightly elevated temperature may also be employed.

In a similar manner, the compound of the general formula III is then reacted with an insulin B-chain, at a pH value in the range of from about 8 to 11, or with the addition of a tertiary organic base, such, for example, as N-ethyl-morpholine, in DMSO or DMF, and the compounds obtained have the general formula IV

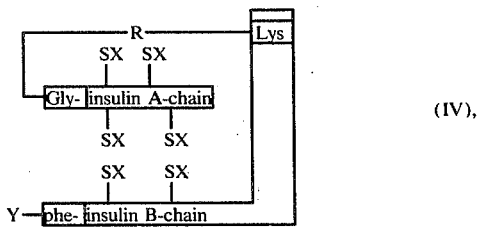

in which R and Y have the meanings given above. As the N-protective group (Y) there are mentioned, for example, tert.-butyloxycarbonyl (Boc)-, phthaloyl-, tolyl- and/or methylsulfonylethyloxycarbonyl- or trifluoroacetyl radicals.

If Y represents an N-protective group, the above reaction sequence may also be reversed, i.e., linkage with the B-chain is the first to be performed, followed by the linkage with the A-chain.

After the protective groups, if any, have been split off and the product has been purified by chromatography, if necessary, the reaction product is dissolved in an 8M aqueous urea solution or water at a pH of from 5 to 9. If X represents, for example, —SO₃H, a 50- to 100-fold excess of thioglycol or 1 to 5 times the calculated amount of a trialkyl phosphine, for example, tributyl phosphine, is added under a nitrogen atmosphere at 0° to 60° C; when the reduction is complete, the mixture is precipitated with acetic acid/acetone, the precipitate is centrifuged and washed several times with acetic acid/acetone. It is then dissolved in the smallest possible amount of aqueous $NH_3$ and diluted with 0.05 M $(NH_4)HCO_3$, adjusted to a pH of from 10 to 10.6, to reach a peptide concentration of from 0.01 to 1 mg/ml. The solution is then stirred overnight at 0° to 20° C in a slow air current. It is also possible to work at a lower pH, for example in the range of from 8 to 10, but then longer reaction times of up to 150 hours may be required. The pH is then adjusted to 4 to 5.5 with 1N acetic acid, and the resulting compound of the general formula I is lyophilized or evaporated to dryness in vacuo. The raw product is purified by way of partition chromatography using Sephadex LH 20 in the system of n-butanol/glacial acetic acid/water (2 : 1 : 10), or via Sephadex G 50 and/or G 75 with 1N to 2N acetic acid (column size : 4 × 100 to 4 × 200 cm). The "insulin peak" (up to about 70%) may be processed in the manner described below, the product that has been combined in the wrong way (up to about 30%) being recycled by a reduction and recombination process.

The elimination of the radical R from the compounds of the general formula I according to the invention is carried out, for example, by a short-time treatment of the product with 0.2N to 1N NaOH at 0° C. To this effect, the compound of the general formula I is dissolved in $H_2O$, optionally while adding dimethylformamide, the solution is then cooled to 0° C and the desired normality is adjusted with ice-cold sodium hydroxide solution. After 2 to 10 minutes, preferably 2 to 3 minutes, the solution is neutralized, while being cooled, with the equivalent amount of 1N HCl. The solvent is distilled off in vacuo. The residue and/or precipitate is dissolved in a small amount of dilute acetic acid, and the solution is chromatographed on Sephadex G 50 or G 75.

Elution may be performed with dilute acetic acid, the insulin-containing fractions are combined, and the pH is adjusted to 5.2, whereupon the insulin that has first precipitated in an amorphous form crystallizes within several hours.

The yield is about 50%, calculated on the insulin A- and B-chains used.

The crystallized insulin obtained according to the invention has a biological activity of 24 to 25 I.U./mg as evaluated by measuring the reduction of the blood sugar level on rabbits. The amino acid analysis corresponds to the calculated value.

The present invention also provides processes for the preparation of insulin analogs and derivatives, besides insulin itself. By insulin analogs there are to be understood compounds in which one or more amino acids are exchanged for other, preferably simpler, amino acids, and/or in which the chain length is modified, preferably shortened.

For example, as already known in the literature, there may be replaced in the A-chain: $Gln^5$ and $Gln^{15}$ by Glu; $Ser^{12}$, $Tyr^{14}$, $Asn^{18}$ and $Asn^{21}$ by Ala; $Val^{10}$ by Leu or another hydrophobic amino acid; moreover, $Tyr^{19}$ may be replaced by Phe.

In the B-chain, there may be replaced $Phe^1$, $Val^2$, $Asn^3$, $Gln^4$, $His^5$, $Ser^9$, $His^{10}$, $Thr^{27}$ and $Pro^{28}$ by simpler amino acids, preferably by alanine. Any one or more of amino acids 1 to 4 and 30 may be eliminated. Even $Cys^{A7}$ and $Cys^{B7}$ may be replaced by Ala.

Insulin derivatives are compounds having substituted functional groups. For example, the α-amino group of the B-chain may be substituted by an acyl group as disclosed in German Offenlegungsschrift No. 2,042,299. The same is true for the above-defined insulin analogs.

Since the substitution of the α-amino group of the insulin B-chain by any group represented by Y is not critical for the biological activity, Y may represent not only one of the N-protective groups usual in peptide chemistry, but also any physiologically acceptable acyl group which has, however, to be limited in its size. For example, for aliphatic alkanoyl or alkyloxycarbonyl groups, this limit is about 6 carbon atoms, for a cycloalkanoyl group or the radical of an aromatic or heterocyclic carboxylic acid it is about 10 carbon atoms. Y may also stand for aminoacyl groups of the naturally occurring α-amino acids or the D-enantiomers and ω-aminocarboxylic acids thereof having up to about 6 carbon atoms, as well as their N-alkanoyl or N-alkyloxycarbonyl compounds having up to about 4 carbon atoms, a cycloalkanoyl group or the radicals of aromatic or heterocyclic carboxylic acids having up to 7 carbon atoms.

Only such substituents are appropriate which do not decrease the biological activity of the insulins or decrease it only to a minor extent. Biological activity not only includes a lowering of the blood sugar level, but also, for example, the ability of these compounds to serve as haptens for antibodies if present.

The insulin or the analogs and derivatives thereof obtained according to the process of the invention may be used, instead of the material recovered from the pancreas, for the treatment of diabetes mellitus in human patients and/or they are used generally in order to lower the blood sugar level, for example in order to produce shock.

The insulin A- and B-chains may be prepared according to one of the numerous methods described in the art. To demonstrate the process of the invention, it is simpler to start from natural chains which can be easily obtained from insulin, for example by sulfitolysis. The insulin chains prepared by synthesis behave like the natural material. This applies also to modified chains, provided these chains still possess the decisive structural characteristics for the biological activity of the insulin prepared therefrom.

The reagents of the general formula II are prepared by reacting the known sulfonyldiethanol with phosgene and converting the dichloro-carbonic acid-ester into the desired activated ester, for example, bis-N-hydroxy-succinimide ester. Another method to prepare the said reagents uses the known chlorocarbonic acid esters of the activated esters as starting products. They are reacted in pyridine with the sulfonyldiethanol according to known methods.

The following reaction schemes illustrate these reaction sequences:

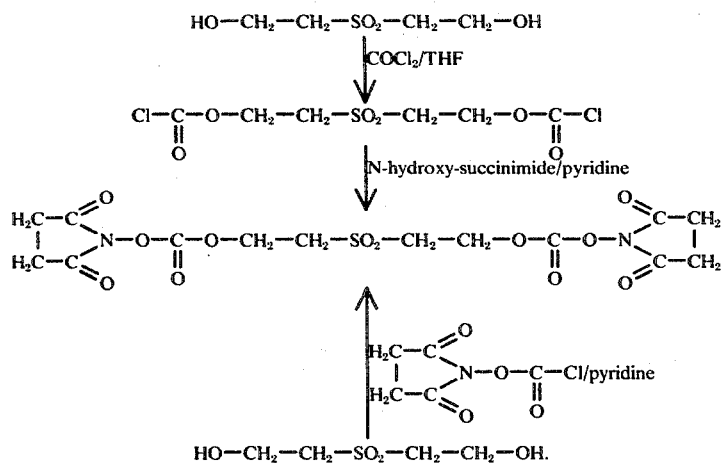

The following Examples serve to illustrate the invention.

EXAMPLE 1

Preparation of the bridging reagent a. Sulfonyldiethyl-bis-oxycarbonyl-di-N-hydroxy-succinate 15.4 g of sulfonyl-diethanol prepared according to J.Org.Chem. 28, 1140 (1963) were dissolved in 90 ml of tetrahydrofurane and were added dropwise within 30 minutes, while stirring, to a solution of 22 g of phosgene in 200 ml of tetrahydrofurane. The temperature was maintained at −10° to −15° C. The mixture was continued to be stirred for 30 minutes at −10° C, and then at room temperatue for another hour. The solvent was distilled off in vacuo. 26 grams of a viscous oil were obtained.

The said oil was dissolved in 27 ml of tetrahydrofurane and 150 ml of methylene-chloride, and a solution consisting of 12 ml of pyridine, 17 g of N-hydroxy-succinimide and 52 ml of methylene-chloride was added dropwise, while stirring, to the mixture at −10° C in the course of 15 minutes. The reaction mixture was stored for 15 hours at +4° C, in which process the reaction product which precipitated at first in the form of an oil became crystallized. It was filtered off, was washed with ice-cold tetrahydrofurane and dried. It had a melting point of from 134° to 137° C (degradation). The elemental analysis correspond to the calculated values.

EXAMPLE 2

Bovine insulin a. Bovine insulin A-chain tetrasulfonate

This compound was prepared from bovine insulin in known manner, for example according to Z. Naturforsch. 18b (1963), page 978.

b. $N^{B1}$-trifluoroacetyl-B-chain disulfonate (bovine)

This compound was also prepared in the usual way by sulfitolysis of $N^{B1}$-trifluoroacetyl insulin (bovine). The latter starting material was obtained as follows:

$N^{\alpha\ A1}$, $N^{\epsilon\ B29}$-bis-Boc-insulin prepared according to Hoppe Seyler's Z. Physiol. Chem. 352 (1971), page 1487, was dissolved in dimethylformamide, and the solution was reacted with about 5 equivalents of trifluoroacetic acid-methyl ester, thus yielding $N^{\alpha\ A1}$, $N^{\epsilon\ B29}$-bis-boc-$N^{\alpha\ B1}$-trifluoroacetyl insulin (bovine). After the Boc-groups had been split off by a 45-minute treatment with trifluoroacetic acid, the product was purified by partition chromatography using Sephadex LH-20 in a system of n-butanol/glacial acetic acid/water (2 : 1 : 10).

c. Bovine insulin

The pH value of a solution of 2.82 g of the A-chain tetrasulfonate prepared under 2a) in 200 ml of dimethylsulfoxide was adjusted to about 9 by adding 1.11 ml of N-ethyl-morpholine, and the mixture was stirred with 1.4 g of the N-hydroxy-succinimide ester prepared according to Example 1c). After 20 hours, the product was precipitated with a 10 : 1 mixture of ether and methanol.

The precipitate was then dissolved in 200 ml of dimethylsulfoxide, 3.45 g of the $N^{B1}$-trifluoroacetyl-B-chain disulfonate prepared under 2b) and 1.1 ml of N-ethylmorpholine were added, and the mixture was stirred for 6 to 24 hours at room temperature. The product was then precipitated with a 10 : 1 mixture of ether and methanol. Yield: 5.2 g.

Upon chromatography in a column using Sephadex G 50 (column size: 4 m in length and 4 cm in diameter) in 0.05M $(NH_4)HCO_3$ buffer solution of pH 8.5 to 9 and lyophilization, the product was dissolved in 0.25 l of water at pH 8.6. 50 ml of thioglycol were added, the mixture was stored for 6 hours under a nitrogen atmosphere, then precipitated with 10 to 20 times its amount of acetic acid/acetone, centrifuged and washed with acetic acid/acetone until free of thioglycol. The product was then dissolved in a small amount of 1N $NH_3$, diluted to 25 l, the pH value was adjusted to 9, and the solution was stirred for about 100 hours in a slight air stream at room temperature.

Under these conditions, the trifluoroacetyl group was split off at the same time. The pH was adjusted to 5.5 with acetic acid, and the solution was lyophilized.

The residue was dissolved in 50 ml of 10 % acetic or formic acid and chromatographed through a column, sized 4 × 200 cm, using Sephadex G 50 or 75, fine. Partition chromatography using Sephadex LH 20 in a system of n-butanol/acetic acid/water (2 : 1 : 10) also allowed a good purification (column size: 4 × 100 to 4 × 200 cm). The columns had been calibrated wit crosslinked insulin. After a preliminary peak (0.3 g) had passed through, the main fraction (4.2 g) was obtained. The isolated material of the preliminary peak was reduced according to J. Am. Chem. Soc. 93 (1971), page 3080, using 1,4-dithiothreitol in liquid $NH_3$ or tributyl-phosphine in dilute aqueous $NH_3$, at pH 8 to 10, and oxidized in water at pH 9 in the manner described above.

In order to split off the cross-linking reagent, the product was dissolved in 75 ml of a mixture of water and dimethylformamide (2 : 1), the solution was cooled to 0° C, and 25 ml of ice-cold 4N NaOH were added. After 2 to 5 minutes, the mixture was neutralized with 50 ml of 2N HCl, while cooling intensively, and the solvent was distilled off in vacuo. The residue was dissolved in 10% acetic acid and was purified in a column (4 × 200 cm) using Sephadex G 50; as eluting agent, use was made of 10% acetic acid. The fractions containing insulin were combined, concentrated in vacuo to a volume of about 40 ml, the pH thereof was adjusted to 5.2 by adding a small amount of $ZnCl_2$, and the substance was allowed to stand for 1 day at room temperature. The resulting crystals were separated by centrifuging the material from non-crystallizing material, and crystallization was repeated. Yield: 2.97 g (49%). The biological activity of the insulin was 25 I.U./mg.

We claim:
1. A method for making an insulin compound of the formula

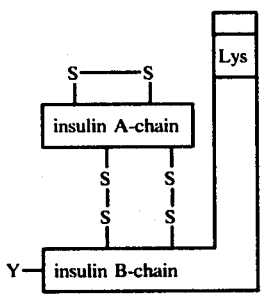

and biologically-active analogs thereof in which one or more amino acids have been exchanged for other, preferably simpler, amino acids or in which the chains are modified, preferably shortened, and in which Y is hydrogen or acyl, which method comprises treating a compound of the formula

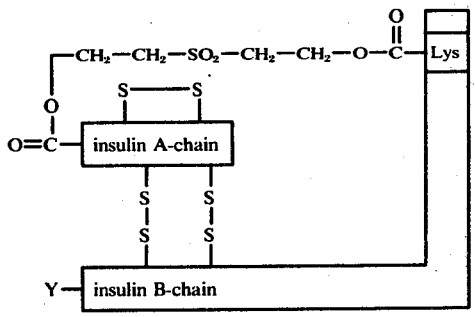

or an analog thereof as hereinbefore defined, with an alkali metal hydroxide or a quaternary organic base having a pH of more than 13.

2. An insulin compound of the formula

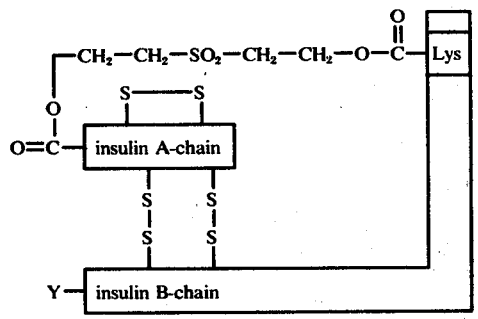

and biologically-active analogs thereof in which one or more amino acids have been exchanged for other, preferably simpler, amino acids or in which the chains are modified, preferably shortened, and in which Y is hydrogen or acyl.

* * * * *